(12) United States Patent
Gaitini

(10) Patent No.: US 6,626,169 B2
(45) Date of Patent: Sep. 30, 2003

(54) ANATOMICAL AIRWAY VENTILATION INTUBATING AND RESUSCITATION DEVICE

(75) Inventor: Luis Gaitini, Haifa (IL)

(73) Assignee: Elisha Medical Technologies Ltd., Katzrin (IL)

( * ) Notice: Subject to any disclaimer, the term of this patent is extended or adjusted under 35 U.S.C. 154(b) by 0 days.

(21) Appl. No.: 09/858,598

(22) Filed: May 17, 2001

(65) Prior Publication Data
US 2002/0170556 A1 Nov. 21, 2002

(51) Int. Cl.[7] .............................................. A61M 16/00
(52) U.S. Cl. ......................... 128/200.14; 128/202.27; 128/207.14; 128/206.26; 128/10; 128/11
(58) Field of Search ................. 128/202.27, 207.14, 128/206.26, 207.15, 205.25, 203.16, 207.18, 207.29, 200.26, 10, 11

(56) References Cited

U.S. PATENT DOCUMENTS

| | | | | |
|---|---|---|---|---|
| 4,231,365 A | * | 11/1980 | Scarberry | 128/207.15 |
| 4,256,099 A | * | 3/1981 | Dryden | 128/200.26 |
| 4,497,318 A | * | 2/1985 | Donmichael | 128/202.28 |
| 4,688,568 A | * | 8/1987 | Frass et al. | 128/202.28 |
| 4,832,020 A | * | 5/1989 | Augustine | 128/207.14 |
| 5,042,469 A | * | 8/1991 | Augustine | 128/200.26 |
| 5,339,808 A | * | 8/1994 | Don Michael | 128/207.15 |
| 5,443,063 A | * | 8/1995 | Greenberg | 128/200.26 |
| 5,499,625 A | * | 3/1996 | Frass et al. | 128/200.26 |
| 5,513,627 A | * | 5/1996 | Flam | 128/200.26 |
| 5,623,924 A | * | 4/1997 | Lindenman et al. | 128/200.26 |
| 5,682,880 A | * | 11/1997 | Brain | 128/200.26 |
| 5,694,929 A | * | 12/1997 | Christopher | 128/205.25 |
| 5,865,176 A | * | 2/1999 | O'Neil | 128/207.14 |
| 5,890,488 A | * | 4/1999 | Burden | 128/200.26 |
| 5,896,858 A | * | 4/1999 | Brain | 128/207.15 |
| 5,957,134 A | * | 9/1999 | Lee | 128/207.14 |
| 2001/0001957 A1 | * | 5/2001 | Allgeyer | 128/207.15 |
| 2001/0012923 A1 | * | 8/2001 | Christopher | 604/48 |
| 2001/0032646 A1 | * | 10/2001 | Christopher | 128/200.26 |
| 2001/0054425 A1 | * | 12/2001 | Bertram | 128/207.15 |

* cited by examiner

Primary Examiner—Gregory L. Huson
Assistant Examiner—Azadeh Kokabi
(74) Attorney, Agent, or Firm—Eitan, Pearl, Latzer & Cohen, Zedek, LLP

(57) ABSTRACT

An anatomically-shaped airway ventilation and intubating device is disclosed, which may comprise a flexible elongated conduit adapted to fit in a patient's oropharynx. The conduit may be partially divided into an intubation lumen and a ventilation lumen, having apertures at the proximal end of the conduit. The distl end of the conduit may be substantially opposite the esophagus opening of the patient when the device is inserted into the oropharynx. The ventilation and intubation lumens may be in fluid communication with an aperture located between the proximate end and the distal end of the conduit, which aperture may be substantially opposite the laryngeal opening of the patient when the device is inserted into the oropharynx.

15 Claims, 3 Drawing Sheets

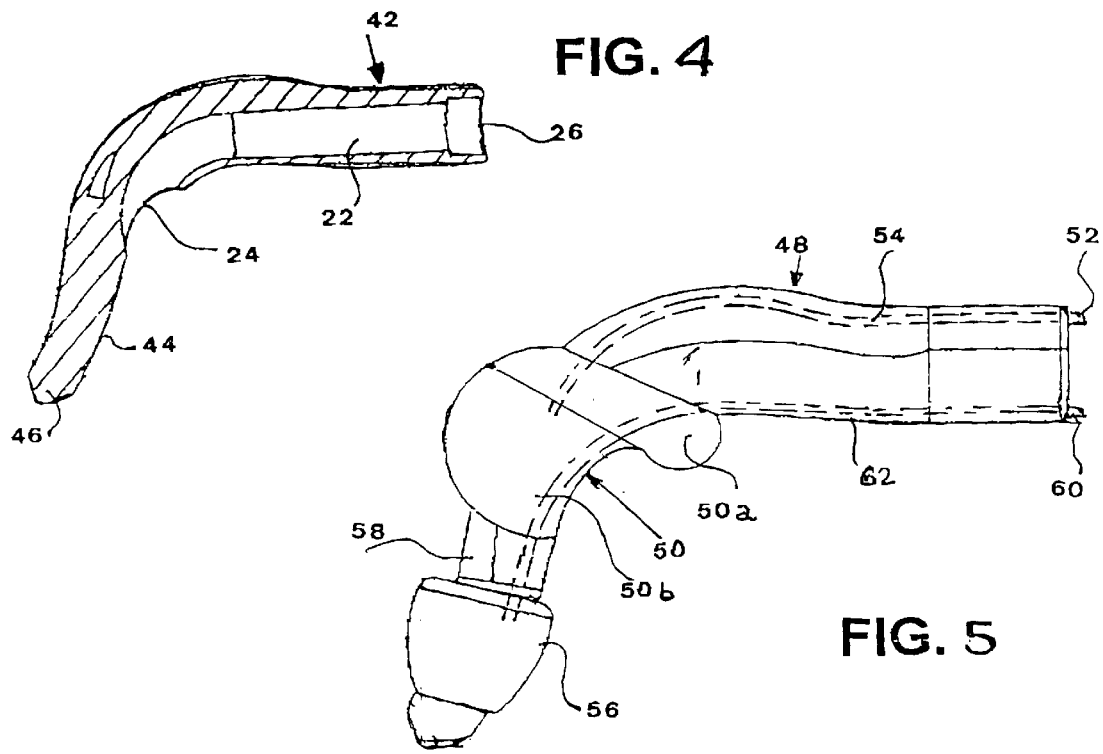
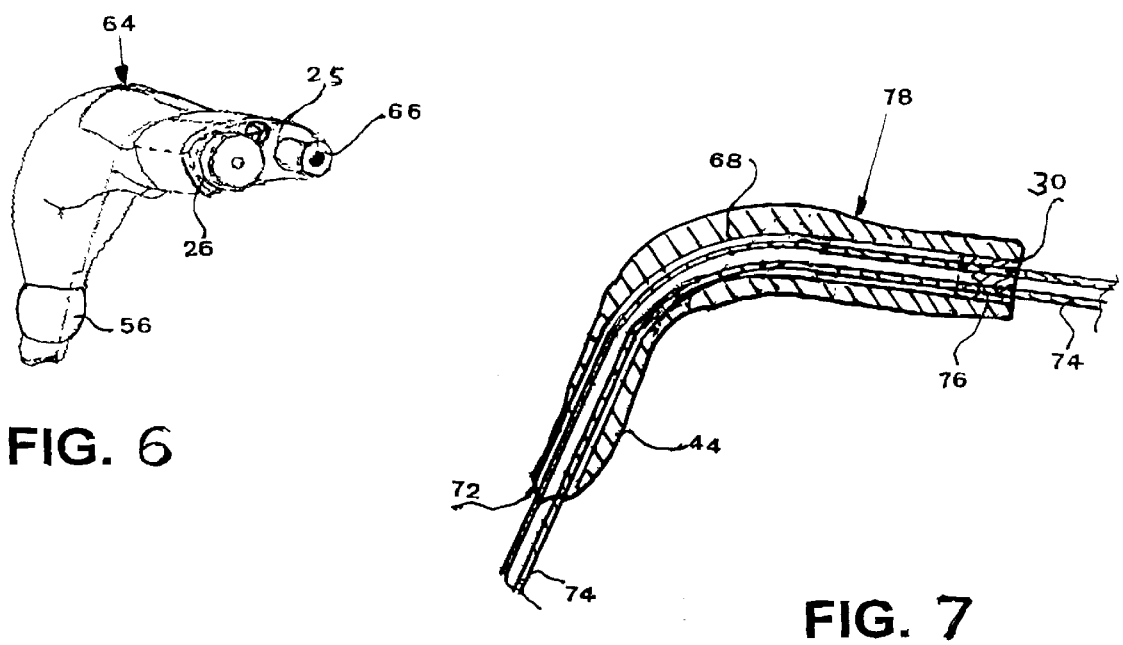

ANATOMICAL AIRWAY VENTILATION INTUBATING AND RESUSCITATION DEVICE

FIELD OF INVENTION

The present invention relates to ventilation and intubation, resuscitation and fiber-optic examination of the airway of patients.

More particularly, the invention provides an anatomically shaped ventilation and intubation device which can be used for inserting a tube into the trachea while allowing continuation of breathing, and can additionally be used for the insertion into the trachea of a fiber-optic probe, and for the resuscitation of a patient by mouth or by a mechanical ventilation device.

BACKGROUND OF THE INVENTION

In regular practice of general anesthesia physicians use an endotracheal tube, which is a flexible tube made of a plastic material having an inflatable cuff surrounding its distal end. Introducing the endotracheal tube into the trachea is a skilled operation requiring the use of a laryngoscope in order to guide the tube through the larynx and past the vocal cords into the trachea. There is a risk that either the tube or the laryngoscope may damage the soft tissue of die sensitive structure of the larynx.

In some patients it is not possible to see the larynx. To offer an acceptable alternative solution for intubation by anesthesiologists and therapist personnel, many devices have been developed for airway management of patients.

The esophageal obturator airway has been used since 1972. However the efficacy of this device is still questionable. Furthermore, its use has been suspected of causing trauma of the esophagus.

In U.S. Pat. No. 5,499,625 Frass et al. disclose an esophageal-tracheal double lumen airway, similar to the esophageal obturator airway. The Frass device was commercialized under the trade name "COMBITUBE". The airway serves for both sole esophageal obturator ventilation and for endotracheal intubation of a patient. The airway includes two lumens, one distal end being open, the other closed. The basic shape of the part of the device to be inserted is a flexible cylindrical tube, which is forced to conform to the shape of the throat during insertion.

Brain discloses an artificial airway device in U.S. Pat. No. 4,509,514, for use in place of an endotracheal tube to facilitate ventilation of an unconscious patient. A laryngeal mask comprises a tube opening into the interior of the inflatable mask adapted to seal around the larynx inlet. The uses of this device are said to be permitting ventilation, securing patient's airway and preventing inhalation of extraneous matter. The device can also be used for endotracheal intubation.

A Laryngeal-mask airway with guide element, stiffener and fiberoptic access is disclosed by Brain in U.S. Pat. No. 5,682,880. The airway has a conventional distal-end mask structure. An external handle connected to the proximate end of reinforcement elements facilitates installation of the mask. Removal of the reinforcement elements exposes guide passages for fiberoptic devices, which devices help in the correct insertion of an endotracheal tube.

Greenberg introduced the cuffed oro-pharyngeal airway (COPA) in U.S. Pat. No. 5,443,063. The airway is intended to replace a face mask as used in maintaining general anesthesia. The inflatable cuff displaces the patient's epiglottis for more effective gas delivery to the lungs. Greenbergs device however fails to provide an easier way to access the trachea in "cannot intubate/cannot ventilate" situations.

U.S. Pat. No. 5,694,929 Christopher discloses a method and apparatus for ventilation/oxygenation during guided insertion of an endotracheal tube, which is inserted during resuscitation by using a face mask and curved guide. Air/oxygen is supplied through the mask for initial resuscitation. The endotracheal tube is inserted over the distal end of a fiber optic probe. Resuscitation, oxygenation or artificial ventilation continue while the tube and probe are inserted through a flexible port at the proximate end of the curved guide and advanced into the patients airway. The direction of the probe tip can be controlled by the physician. The probe and mask are then removed, leaving the tube in the trachea.

Furthermore, tire resuscitation process is exposed to difficulties while using the face-mask. The incidence of difficult intubation in the general population varies between 1%–18%. Complete failed mask ventilation and endotracheal intubation frequently result in brain damage or death.

The management of the difficult airway was considered by the American Society of Anesthesiology (ASA) In 1991 the ASA developed the "ASA difficult algorithm", which is in continuous development since. The algorithm considers the appropriate options for management of the difficult airway, particularly for "cannot intubate/cannot ventilate" situations.

No prior-art device answers the need for an adequate and reliable solution for airway management, alternative to endotracheal intubation, and particularly the need for simultaneous ventilation/oxygenation of the patient, fiberoptic intubation and prevention of aspiration of the gastric fluid content.

A major shortcoming of prior-art devices is that the device shape is far from being in accordance with the shape of the organs into which they are to be inserted. Thus in addition to the trauma which brought about the need for medical intervention, the patient suffers further pain as the prior-art airway device is inserted and attempts to resume its original form.

It is therefore one of the objects of the present invention to obviate the disadvantages of prior art devices and to provide an anatomically formed airway device which can be used in routine intervention and in cases of difficult introduction, and allows tracheal intubation aided by a fiberoptic probe while providing simultaneous and continuous ventilation or oxygenation, while preventing gastric dilation and preventing aspiration of the gastric fluid content.

It is a further object of the present invention to seal the patient's mouth and nose to allow positive pressure artificial ventilation, if needed.

Yet a further object of the present invention is to adapt the shape of the device to more closely match the shape of the oropharynx so that the device can be substantially painlessly inserted even by paramedics and first-aid personnel.

The present invention achieves the above objects by providing an anatomically-shaped airway ventilation and intubating device, comprising a flexible elongated conduit adapted to fit in a patient's oropharynx, said conduit having a proximate end and a distal end, said conduit being partially divided by a septum into a ventilation lumen and an intubation lumen, said lumens being in fluid communication to a first opening at said distal end to be substantially opposite the laryngeal opening of the patient when inserted, and wherein a second opening is provided at said proximate end, said second opening being in fluid communication with said ventilation lumen; whereby said intubation lumen is adapted to accommodate an endotracheal tube that can be inserted while enabling breathing of patient through said ventilator lumen and whereby after said endotracheal tube is inserted said first opening may be sealed while patient's breathing is directed through said endotracheal tube.

In a preferred embodiment of the present invention there is provided an anatomically-shaped airway intubating device further provided with a third opening in fluid communication with said intubation lumen, said third opening being provided with a valve allowing the insertion therethough of a fiber-optic probe into said intubation lumen.

In a further preferred embodiment of the present invention there is provided an anatomically-shaped airway ventilation and intubating device wherein the two openings of largest diameter are in horizontal side-to-side formation with the smallest of said three openings being located between ad largest openings and spaced apart from the center-line joining said largest openings.

In a further preferred embodiment of the present invention there is provided an anatomically-shaped airway ventilation and intubating device, further provided with an elongated endoesophageal lobe at said distant end adapted to be inserted through the patient's upper esophagus.

In a most preferred embodiment of the present invention there is provided an anatomically-shaped airway resuscitating device, comprising a flexible elongated conduit adapted to fit in a patients oropharynx, said conduit having a proximate end and a distal end, said conduit being partially divided by a septum into an inspiratory lumen and an expiatory lumen, said lumens being in fluid communication to a first opening at said distal end to be substantially opposite the laryngeal opening of the patient when inserted, and wherein a second and a third opening are provided at said proximate end, said second opening being in fluid communication with said inspiratory lumen and said third opening being in fluid communication with said expiatory lumen, said second opening being provided with a one-way valve allowing air to enter said inspiratory lumen.

It will thus be realized that the novel device of the present invention serves to provide an alternative to endotracheal intubation, a procedure which may be impossible, or undesirable during some elective operations, or too risky in difficult cases. Nevertheless, if it is possible and desirable to insert an endotracheal tube, the device of the present invention allows this to be carried out without any interruption of ventilation. Even where intubation is carried out, this will usually be possible without the use of a bronchoscope. If however it is considered necessary to use such instrument, a passage therefor is provided by the airway of the present invention.

Simply by rearranging the positions of the entry ports of the various lumens, the outer dimensions and shape of the device can be much better suited to the natural shape of the oral cavity and pharynx. The device can be produced in various sizes, and color coded, to suit the oropharynx of different sections (children, adults) of the population.

The device can be used in emergency care of cardiac arrest, near drowning, coma, trauma and any circumstances where free airway ventilation is necessary and gastric aspiration must be prevented.

The device is easily inserted, and due to its shaped exterior can even be inserted blindly.

The resuscitator embodiments of the invention are suitable for use in emergency medicine, and insertion of the airway into a patient can be effected by first aid personnel and paramedics, as due to the anatomical shape of the device, no particular skill is required. A doctor is often unavailable in an emergency situation, and in the meantime, a paramedic, a sea or swimming pool life guard, or a civil defense rescue worker, for example, may save a patient by using the airway device by restoring breathing by connecting air or oxygen or the rescue person's breath into the inspiratory lumen while allowing used air containing carbon dioxide to flow out of the expiratory valve.

The invention will now be described further with reference to the accompanying drawings, which represent by example preferred embodiments of the invention. Structural details are shown only as far as necessary for a fundamental understanding thereof. The described examples, together with the drawings, will make apparent to those skilled in the art how further forms of the invention may be realized.

BRIEF DESCRIPTION OF THE DRAWINGS

FIG. 4 is a sectioned elevational view of an embodiment having an elongated endoesophageal lobe;

FIG. 5 is an elevational view of an embodiment provided with two sealing balloons;

FIG. 6 is a perspective view of an embodiment wherein the first opening is fitted with a connector;

FIG. 7 is an elevational sectional view of an embodiment arranged to accept a Zonda tube;

DETAILED DESCRIPTION OF PREFERRED EXEMPLARY EMBODIMENTS

Figure 1:
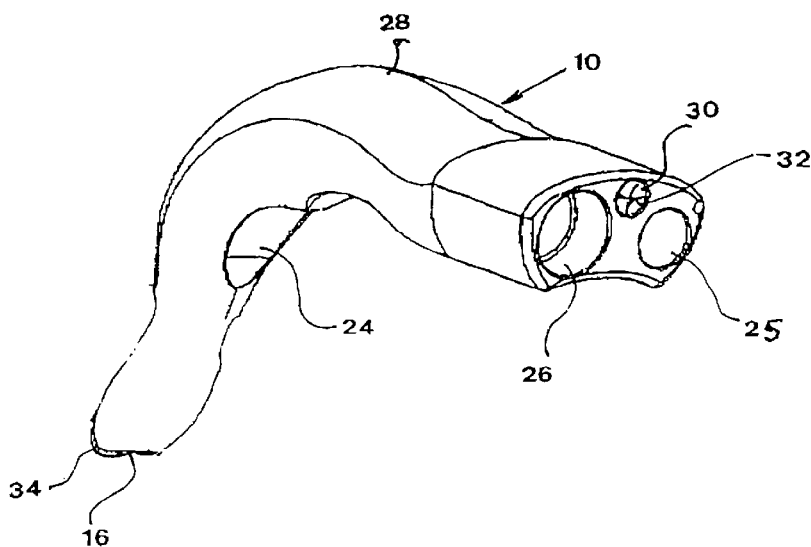
FIG. 1 is a perspective view of a preferred embodiment of the airway intubation device according to the invention.
Figure 2:
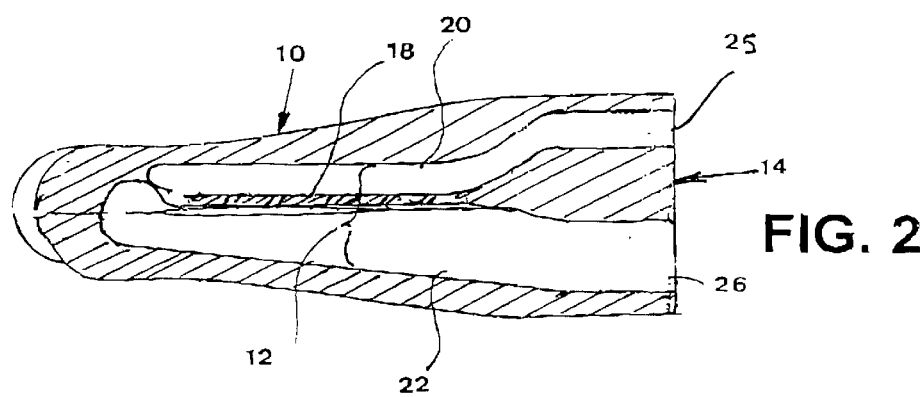
FIG. 2 is a cross-sectional view of the same embodiment taken on a horizontal plane across the lumens having the largest openings.

There is seen in FIGS. 1 and 2 an anatomically-shaped airway intubating device 10, comprising a flexible elongated body adapted to fit in a patient's oropharynx. The body of the device can suitably be cast in silicone rubber, or other medical grade materials colored according to size. For example: red—largest, green for young children, yellow—intermediate size. Thus the physician loses no time in selecting the appropriate device. As seen in FIG. 2, the device 10 has a proximate end 14 and a distal end 16, and is partially divided by a septum 18 into a ventilation lumen 20 and an intubation lumen 22. The septum 18, which is fenestrated to allow airflow between the lumens.

The lumens 20, 22 are in fluid communication with an opening 24 at the distal end thereof which is positioned to be opposite the laryngeal opening of the patient when inserted. A further opening 26 is provided at the proximate end 14, the said opening 26 being in fluid communication with the intubation lumen 22.

The intubation lumen 22 is preferably sized to accept a standard no. 7.5 endotracheal tube (not shown). An additional opening 25 is provided at the proximate end 14. Said opening is adapted to be connected to a ventilation device.

In the preferred embodiment shown, a fourth opening 30 is provided at the proximate end 14, allowing the insertion therethrough of a gastric zonda for draining stomach content. Insertion of an endotracheal tube is possible while enabling breathing of the patient through the lumen 20. After the endotracheal tube is inserted in trachea the opening 24 is practically sealed while patient's breathing is directed through the endotracheal tube. The body of the device 10 is shaped at 28 to fit the patient's oropharynx and to push up the soft palate so as to close the oropharynx from the nasopharynx.

With reference to the rest of the figures, similar reference numerals have been used to identify similar parts.

Figure 3:
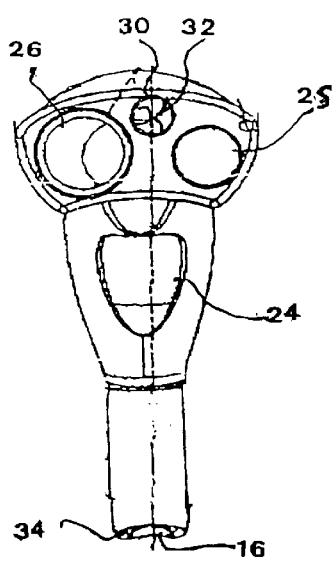
FIG. 3 is an end view of the same embodiment.

FIG. 3 illustrates an important feature of the anatomically-shaped airway ventilation and intubating device. The two proximate openings 25, 26 of largest diameter, i.e. opening 25 which is about 10 mm diameter and used for ventilation, and the other opening 26 which is about 17 mm diameter and is used for intubation, are in horizontal side-to-side formation. Opening 30, i.e. the opening used for insertion of a gastric zonda for draining the stomach content, is located between the largest openings 25, 26 and spaced apart from the center-line joining the largest openings. This arrangement is ideal for maintaining the anatomically correct shape of the device.

Referring now to FIG. 4, there is depicted an anatomically-shaped airway ventilation intubating device 42, further provided with an elongated endoesophageal lobe 44 at its distal end 46. The lobe 44 is adapted to be inserted through, and to block, the patient's upper esophagus. The lobe 44 is provided by a small balloon that can seal the upper part of esophagus. Typical dimensions for the lobe are about 4 cm to 7 cm long and about 2 cm diameter.

FIG. 5 shows an anatomically-shaped airway ventilation device 48, further provided with a first balloon 50. In the preferred embodiment shown the first balloon is formed of a pair of spaced-apart plastic bags, an upper bag 50a and a bag 50b.

Inflation of the bag 50b by means of conduit 54, sealingly blocks the patient's air passage between the nasopharynx and the oropharynx. Inflation of this bag prevents air passage through the nose.

The other bag 50a, when inflated through a first conduit 54 and a port 52 provided at the proximate end of the device, pushes forward the root of the tongue, thus preventing the tongue from obstructing the airway at the laryngeal entry. The port 52 is a connector to a standard syringe to facilitate inflation thereby.

The anatomically-shaped airway intubating device seen in the present figure is further provided with a third balloon 56 adapted to sealingly block the patient's esophagus so as to ensure that stomach fluids do not aspirate, and also to avoid gastric inflation. The third balloon 56 is positioned on the circumference of the endoesophageal lobe 58. The third balloon 56 is inflatable through port 60 or 52 at the proximate end via a second inflation conduit 62. In effect the balloon 56 enlarges the endoesophageal lobe 58, and so fixes the lobe 58 inside the esophagus.

FIG. 6 illustrates an anatomically-shaped airway ventilation device 64 wherein the first opening 25 is provided with a connector 66 adapted for connection to a ventilator device (not shown).

As has already been seen in FIG. 1, the opening 30 is designed to accommodate a gastric zonda.

Seen in FIG. 7 is an anatomically-shaped airway ventilation device 78 provided with a further tube 68 adjacent to the ventilator lumen 20 seen in FIG. 2. The tube 68 has a proximate opening 30 and passes through the endoesophageal lobe 44 and has a distal opening 72 at the end of the esophageal lobe 44. The tube 68 is sized to accommodates a Zonda tube 74, after a seal 76 at the proximate end is removed. The Zonda tube 74 is then inserted into the stomach, The Zonda tube 74 may be used to remove stomach contents.

Figures 8, 9:
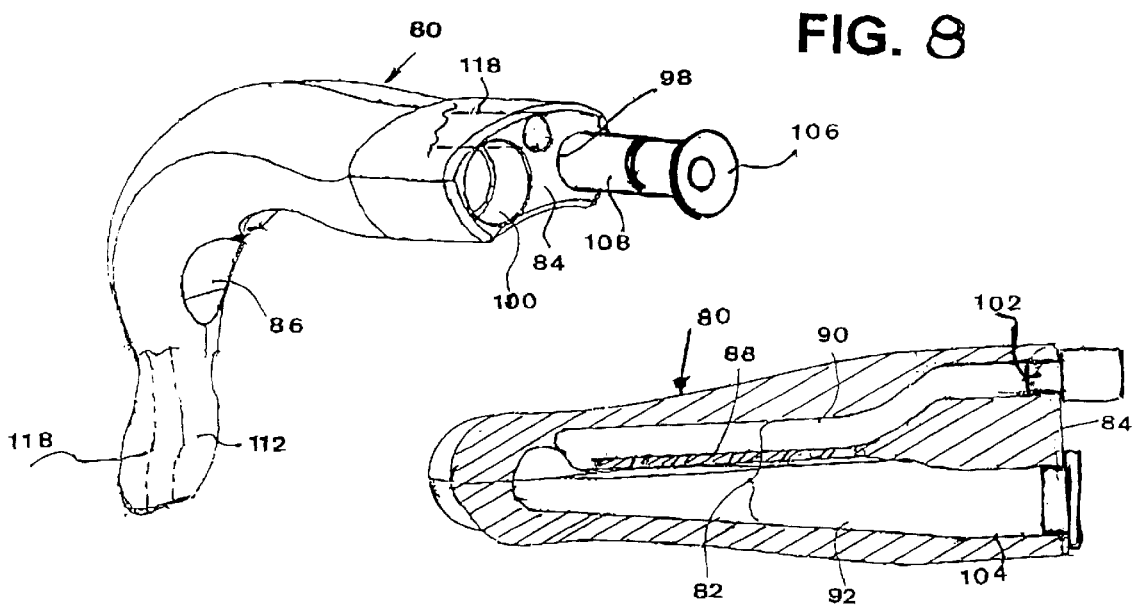
FIG. 8 is a perspective view of an airway resuscitating device.
FIG. 9 is a cross-sectional view of the embodiment of FIG. 9 taken on a horizontal plane across the lumens having the largest openings.

Referring now to FIGS. 8 and 9, there is depicted an anatomically-shaped airway resuscitating device, intended for emergency treatment.

As the device is similar to the ventilation and intubation airway, features similar to the intubation device will be described only in outline to avoid repetitiveness.

The resuscitating device 80 seen in FIGS. 8, 9, comprises a flexible elongated conduit 82 adapted to fit in a patient's oropharynx. The conduit 82 has a proximate end 84 and a distal end 86. The conduit 82 is partially divided by a septum 88 into an inspiratory lumen 90 and an expiratory lumen 92.

The septum 88 extends from the proximate end 84 up to about 2 cm prior to the distal end 86 of the conduit 82.

The lumens 90, 92 are in fluid communication with a first opening at the distal end 86 to be substantially opposite the laryngeal opening of the patient when inserted.

A two openings 98, 100 are provided at the proximate end 84. The opening 98 is in fluid communication with the ventilatory lumen 90. The opening 98 is provided with a one way valve adapter 102 allowing air to enter the inspiratory lumen 90, opening 100 is provided with a closure.

The two openings 98, 100 of largest diameter are in horizontal side-to-side formation.

The second opening 98, leading to the ventilation lumen 90, is provided with a removable extension 106 adapted for resuscitation of the patient by mouth of a medical or rescuing person or resuscitation device. The extension 106 is removable so that when a ventilation device is available, such device can be connected to the same fitting 108 holding the removable extension 106.

An elongated endoesophageal lobe 112 is adapted to be inserted through the patient's upper esophagus.

The scope of the described invention is intended to include all embodiments coming within the meaning of the following claims. The foregoing examples illustrate useful forms of the invention, but are not to be considered as limiting its scope, as those skilled in the art will readily be aware that additional variants and modifications of the invention can be formulated without departing from the meaning of the following claims.

What is claimed is:

1. An airway intubating and ventilation device comprising:
   a flexible elongated conduit adapted to be inserted into a patient's oropharynx, said conduit partially divided into an intubation lumen adapted to accommodate an endotracheal tube and a ventilation lumen, said conduit having a proximate end having a ventilation inlet aperture and an intubation inlet aperture and a distal end substantially opposite the esophagus opening of the patient when the device is inserted into the oropharynx, wherein said lumens are in fluid communication with an aperture located substantially opposite the laryngeal opening of the patient when the device is inserted into the oropharynx.

2. The device as claimed in claim 1, further comprising an elongated endoesophageal lobe at said distal end of the device adapted to be inserted through the patient's upper esophagus.

3. The device as claimed in claim 2, further comprising a gastric lumen having an inlet at a gastric lumen aperture at said proximate end of the device and an outlet at said endoesophageal lobe, wherein said gastric lumen is adapted to accommodate a gastric tube.

4. The device as claimed in claim 3, wherein said ventilation inlet aperture and said intubation inlet aperture are in horizontal side-to-side formation, and wherein the gastric lumen aperture is located between said ventilation inlet aperture and said intubation inlet aperture and spaced apart from the center-line joining said ventilation inlet aperture and said intubation inlet aperture.

5. The device as claimed in claim 1, further comprising a nasopharyngeal balloon on the exterior of said device adapted to sealingly block the patient's air passage between the nasopharynx and the oropharynx, said nasopharyngeal balloon being inflatable through a balloon port near said proximate end of the device via a balloons inflation conduit.

6. The device as claimed in claim 5, wherein said nasopharyngeal balloon is adapted to prevent the tongue from obstructing the airway at the laryngeal entry.

7. The device as claimed in claim 1, further comprising an esophageal balloon on the exterior of said device adapted to sealingly block the patient's esophagus, said esophageal balloon being inflatable through a balloon port near said proximate end of the device via a balloon inflation conduit.

8. The device as claimed in claim 7, wherein said esophageal balloon is positioned on the circumference of said endoesophageal lobe so that when said esophageal balloon is inflated, said endoesophageal lobe is retained inside the patient's esophagus.

9. The device as claimed in claim 1, further comprising a septum partially dividing said conduit into said ventilation lumen and said intubation lumen.

10. The device as claimed in claim 7, wherein said septum is fenestrated to allow airflow between said lumens.

11. The device as claimed in claim 1, wherein said conduit is anatomically shaped to fit the patient's oropharynx and to push up the soft palate to close the oropharynx from the nasopharynx.

12. The device as claimed in claim 1, wherein said ventilation inlet aperture is adapted for connection to a ventilator device.

13. The device as claimed in claim 1, further comprising a lid adapted to fit said intubation inlet aperture.

14. The device as claimed in claim 1, further comprising a one-way valve associated with said ventilation inlet aperture.

15. The device as claimed in claim 1, further comprising a removable extension for said ventilation inlet aperture adapted for resuscitation of the patient by mouth.

* * * * *